(12) United States Patent
Kirma et al.

(10) Patent No.: US 9,474,440 B2
(45) Date of Patent: Oct. 25, 2016

(54) ENDOSCOPE TIP POSITION VISUAL INDICATOR AND HEAT MANAGEMENT SYSTEM

(71) Applicant: EndoChoice, Inc., Alpharetta, GA (US)

(72) Inventors: Yaniv Kirma, Karcur (IL); Yuri Gershov, Haifa (IL); Avi Levy, Herzliya (IL); Golan Salman, Atlit (IL)

(73) Assignee: EndoChoice, Inc., Alpharetta, GA (US)

( * ) Notice: Subject to any disclaimer, the term of this patent is extended or adjusted under 35 U.S.C. 154(b) by 203 days.

(21) Appl. No.: 14/274,323

(22) Filed: May 9, 2014

(65) Prior Publication Data

US 2014/0296628 A1    Oct. 2, 2014

Related U.S. Application Data

(63) Continuation-in-part of application No. 13/984,028, filed as application No. PCT/IL2012/050037 on Feb. 6, 2012, now Pat. No. 9,101,266, application No. 14/274,323, which is a continuation-in-part of (Continued)

(51) Int. Cl.
| | |
|---|---|
| *A61B 1/04* | (2006.01) |
| *H04N 9/47* | (2006.01) |
| *H04N 7/18* | (2006.01) |
| *A61B 1/12* | (2006.01) |
| *A61B 1/06* | (2006.01) |
| *A61B 5/06* | (2006.01) |

(52) U.S. Cl.
CPC ............. *A61B 1/128* (2013.01); *A61B 1/0676* (2013.01); *A61B 1/0684* (2013.01); *A61B 5/064* (2013.01)

(58) Field of Classification Search
None
See application file for complete search history.

(56) References Cited

U.S. PATENT DOCUMENTS

| | | |
|---|---|---|
| 4,027,697 A | 6/1977 | Bonney |
| 4,084,401 A | 4/1978 | Belardi |
| 4,402,313 A | 9/1983 | Yabe |
| 4,461,282 A | 7/1984 | Ouchi |
| 4,494,549 A | 1/1985 | Namba |
| 4,532,918 A | 8/1985 | Wheeler |

(Continued)

FOREIGN PATENT DOCUMENTS

| | | |
|---|---|---|
| CA | 2297986 | 3/1999 |
| CA | 2765559 | 12/2010 |

(Continued)

OTHER PUBLICATIONS

International Search Report for PCT/US2014/037526, Oct. 16, 2014.

(Continued)

*Primary Examiner* — Frederick Bailey
*Assistant Examiner* — Talha M Nawaz
(74) *Attorney, Agent, or Firm* — Novel IP

(57) ABSTRACT

The present specification discloses an endoscope having a tip section equipped with multiple viewing elements. Each of the viewing elements' field of view is illuminated by a discrete illuminator, such as a LED, being operated in a flash mode. The flash mode of operation of the LEDs enable doctors to obtain a position of the endoscope tip within a patient's body from outside by viewing the light emitted by the LEDs. Since the light is emitted for short pre-defined periods of time, the heat generated by the LEDs during their periods of operation is within a safe threshold value, and does not cause any burn injury inside the patient's body.

20 Claims, 9 Drawing Sheets

Related U.S. Application Data application No. 13/992,021, filed as application No. PCT/IL2011/050050 on Dec. 8, 2011, now Pat. No. 9,320,419, application No. 14/274,323, which is a continuation-in-part of application No. 13/992,014, filed as application No. PCT/IL2011/050049 on Dec. 8, 2011, application No. 14/274,323, which is a continuation-in-part of application No. 13/882,004, filed as application No. PCT/IL2011/000832 on Oct. 27, 2011, now abandoned, application No. 14/274,323, which is a continuation-in-part of application No. 13/822,908, filed as application No. PCT/IL2011/000745 on Sep. 20, 2011, application No. 14/274,323, which is a continuation-in-part of application No. 13/713,449, filed on Dec. 13, 2012, and a continuation-in-part of application No. 13/655,120, filed on Oct. 18, 2012, which is a continuation-in-part of application No. 13/119,032, filed as application No. PCT/IL2010/000476 on Jun. 16, 2010, application No. 14/274,323, which is a continuation-in-part of application No. 13/212,627, filed on Aug. 18, 2011, which is a continuation-in-part of application No. 13/119,032, filed on Jul. 15, 2011, application No. 14/274,323, which is a continuation-in-part of application No. 13/413,252, filed on Mar. 6, 2012, now Pat. No. 9,101,287, and a continuation-in-part of application No. 13/413,141, filed on Mar. 6, 2012, now Pat. No. 8,926,502, and a continuation-in-part of application No. 13/413,059, filed on Mar. 6, 2012, now Pat. No. 9,402,533, and a continuation-in-part of application No. 13/412,974, filed on Mar. 6, 2012, now abandoned.

(60) Provisional application No. 61/822,805, filed on May 13, 2013, provisional application No. 61/439,948, filed on Feb. 7, 2011, provisional application No. 61/421,240, filed on Dec. 9, 2010, provisional application No. 61/421,238, filed on Dec. 9, 2010, provisional application No. 61/407,495, filed on Oct. 28, 2010, provisional application No. 61/384,354, filed on Sep. 20, 2010, provisional application No. 61/569,796, filed on Dec. 13, 2011, provisional application No. 61/218,085, filed on Jun. 18, 2009, provisional application No. 61/449,746, filed on Mar. 7, 2011, provisional application No. 61/449,743, filed on Mar. 7, 2011, provisional application No. 61/449,741, filed on Mar. 7, 2011, provisional application No. 61/449,739, filed on Mar. 7, 2011.

(56) References Cited

U.S. PATENT DOCUMENTS

| | | | |
|---|---|---|---|
| 4,588,294 | A | 5/1986 | Siegmund |
| 4,641,635 | A | 2/1987 | Yabe |
| 4,727,859 | A | 3/1988 | Lia |
| 4,764,001 | A | 8/1988 | Yokota |
| 4,801,792 | A | 1/1989 | Yamasita |
| 4,825,850 | A | 5/1989 | Opie |
| 4,877,314 | A | 10/1989 | Kanamori |
| 4,902,115 | A | 2/1990 | Takahashi |
| 4,976,522 | A | 12/1990 | Igarashi |
| 4,984,878 | A | 1/1991 | Miyano |
| 5,007,406 | A | 4/1991 | Takahashi |
| 5,014,685 | A | 5/1991 | Takahashi |
| 5,193,525 | A | 3/1993 | Silverstein |
| 5,224,929 | A | 7/1993 | Remiszewski |
| 5,296,971 | A | 3/1994 | Mori |
| 5,359,456 | A | 10/1994 | Kikuchi |
| 5,395,329 | A | 3/1995 | Fleischhacker |
| 5,447,148 | A | 9/1995 | Oneda |
| 5,460,167 | A | 10/1995 | Yabe |
| 5,464,007 | A | 11/1995 | Krauter |
| 5,489,256 | A | 2/1996 | Adair |
| 5,518,501 | A | 5/1996 | Oneda |
| 5,518,502 | A | 5/1996 | Kaplan |
| 5,547,457 | A | 8/1996 | Tsuyuki |
| 5,575,755 | A | 11/1996 | Krauter |
| 5,587,839 | A | 12/1996 | Miyano |
| 5,630,782 | A | 5/1997 | Adair |
| 5,662,588 | A | 9/1997 | Iida |
| 5,674,182 | A | 10/1997 | Suzuki |
| 5,685,823 | A | 11/1997 | Ito |
| 5,702,347 | A | 12/1997 | Yabe |
| 5,707,344 | A | 1/1998 | Nakazawa |
| 5,725,474 | A | 3/1998 | Yasui |
| 5,725,476 | A | 3/1998 | Yasui |
| 5,725,477 | A | 3/1998 | Yasui |
| 5,725,478 | A | 3/1998 | Saad |
| 5,777,797 | A | 7/1998 | Miyano |
| 5,782,751 | A | 7/1998 | Matsuno |
| 5,810,715 | A | 9/1998 | Moriyama |
| 5,836,894 | A | 11/1998 | Sarvazyan |
| 5,860,913 | A | 1/1999 | Yamaya |
| 5,870,234 | A | 2/1999 | EbbesmeierneeSchitthof |
| 5,916,148 | A | 6/1999 | Tsuyuki |
| 5,940,126 | A | 8/1999 | Kimura |
| 6,095,970 | A | 8/2000 | Hidaka |
| 6,117,068 | A | 9/2000 | Gourley |
| 6,181,481 | B1 | 1/2001 | Yamamoto |
| 6,196,967 | B1 | 3/2001 | Lim |
| 6,261,226 | B1 | 7/2001 | McKenna |
| 6,277,064 | B1 | 8/2001 | Yoon |
| 6,359,674 | B1 | 3/2002 | Horiuchi |
| 6,375,610 | B2 | 4/2002 | Verschuur |
| 6,402,738 | B1 | 6/2002 | Ouchi |
| 6,419,626 | B1 | 7/2002 | Yoon |
| 6,476,851 | B1 | 11/2002 | Nakamura |
| 6,638,214 | B2 | 10/2003 | Akiba |
| 6,673,012 | B2 | 1/2004 | Fujii |
| 6,712,760 | B2 | 3/2004 | Sano |
| 6,832,984 | B2 | 12/2004 | Stelzer |
| 6,888,119 | B2 | 5/2005 | Iizuka |
| 7,435,218 | B2 | 10/2008 | Krattiger |
| 7,621,869 | B2 | 11/2009 | Ratnakar |
| 7,630,148 | B1 | 12/2009 | Yang |
| 7,701,650 | B2 | 4/2010 | Lin |
| 7,713,246 | B2 | 5/2010 | Shia |
| 7,746,572 | B2 | 6/2010 | Asami |
| 7,813,047 | B2 | 10/2010 | Wang |
| 7,828,725 | B2 | 11/2010 | Maruyama |
| 7,927,272 | B2 | 4/2011 | Bayer |
| 7,967,745 | B2 | 6/2011 | Gilad |
| 7,976,462 | B2 | 7/2011 | Wright |
| 8,064,666 | B2 | 11/2011 | Bayer |
| 8,182,422 | B2 | 5/2012 | Bayer |
| 8,197,399 | B2 | 6/2012 | Bayer |
| 8,235,887 | B2 | 8/2012 | Bayer |
| 8,262,558 | B2 | 9/2012 | Sato |
| 8,287,446 | B2 | 10/2012 | Bayer |
| 8,289,381 | B2 | 10/2012 | Bayer |
| 8,300,325 | B2 | 10/2012 | Katahira |
| 8,310,530 | B2 | 11/2012 | Bayer |
| 8,447,132 | B1 | 5/2013 | Galil |
| 8,449,457 | B2 | 5/2013 | Aizenfeld |
| 8,585,584 | B2 | 11/2013 | Ratnakar |
| 8,587,645 | B2 | 11/2013 | Bayer |
| 8,672,836 | B2 | 3/2014 | Higgins |
| 8,715,168 | B2 | 5/2014 | Ratnakar |
| 8,797,392 | B2 | 8/2014 | Bayer |
| 8,872,906 | B2 | 10/2014 | Bayer |
| 8,926,502 | B2 | 1/2015 | Levy |
| 9,044,185 | B2 | 6/2015 | Bayer |
| 9,101,266 | B2 | 8/2015 | Levi |
| 9,101,268 | B2 | 8/2015 | Levy |
| 9,101,287 | B2 | 8/2015 | Levy |
| 9,314,147 | B2 | 4/2016 | Levy |
| 9,320,419 | B2 | 4/2016 | Kirma |

(56) References Cited

U.S. PATENT DOCUMENTS

| | | |
|---|---|---|
| 2001/0036322 A1 | 11/2001 | Bloomfield |
| 2002/0017515 A1 | 2/2002 | Obata |
| 2002/0047897 A1 | 4/2002 | Sugimoto |
| 2002/0087047 A1 | 7/2002 | Remijan |
| 2002/0109774 A1 | 8/2002 | Meron |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1* | 4/2003 | Iida .................. H04N 7/183 348/65 |
| 2003/0083552 A1 | 5/2003 | Remijan |
| 2003/0128893 A1 | 7/2003 | Castorina |
| 2003/0153897 A1 | 8/2003 | Russo |
| 2004/0015054 A1 | 1/2004 | Hino |
| 2004/0046865 A1 | 3/2004 | Ueno |
| 2004/0061780 A1 | 4/2004 | Huffman |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2005/0018042 A1* | 1/2005 | Rovegno ................ A61B 1/04 348/65 |
| 2005/0020876 A1 | 1/2005 | Shioda |
| 2005/0038317 A1 | 2/2005 | Ratnakar |
| 2005/0047134 A1 | 3/2005 | Mueller |
| 2005/0090709 A1 | 4/2005 | Okada |
| 2005/0096501 A1 | 5/2005 | Stelzer |
| 2005/0119527 A1* | 6/2005 | Banik ............... A61B 1/00059 600/117 |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0283048 A1 | 12/2005 | Gill |
| 2006/0047184 A1 | 3/2006 | Banik |
| 2006/0063976 A1* | 3/2006 | Aizenfeld .......... A61B 1/00096 600/179 |
| 2006/0069314 A1 | 3/2006 | Farr |
| 2006/0114986 A1 | 6/2006 | Knapp |
| 2006/0149129 A1 | 7/2006 | Watts |
| 2006/0171693 A1* | 8/2006 | Todd .................. A61B 1/00029 396/17 |
| 2006/0173245 A1* | 8/2006 | Todd .................. A61B 1/0653 600/178 |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1* | 9/2006 | Thrailkill ............ A61B 1/0676 362/249.06 |
| 2006/0252994 A1 | 11/2006 | Ratnakar |
| 2006/0264704 A1 | 11/2006 | Fujimori |
| 2006/0293556 A1 | 12/2006 | Garner |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1* | 4/2007 | Omori ............... A61B 1/00059 600/101 |
| 2007/0106119 A1 | 5/2007 | Hirata |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | DeLorme |
| 2007/0213591 A1 | 9/2007 | Aizenfeld |
| 2007/0229656 A1 | 10/2007 | Khait |
| 2007/0244353 A1 | 10/2007 | Larsen |
| 2007/0244354 A1 | 10/2007 | Bayer |
| 2007/0247867 A1* | 10/2007 | Hunter ................ A61B 1/0684 362/551 |
| 2007/0265492 A1* | 11/2007 | Sonnenschein .... A61B 1/00059 600/101 |
| 2007/0270642 A1 | 11/2007 | Bayer |
| 2007/0279486 A1 | 12/2007 | Bayer |
| 2007/0293720 A1 | 12/2007 | Bayer |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 9/2008 | Seibel et al. |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1* | 1/2009 | Nicolaou ................ G06T 5/008 600/109 |
| 2009/0054790 A1 | 2/2009 | Czaniera |
| 2009/0062615 A1 | 3/2009 | Yamaya |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0213211 A1 | 8/2009 | Bayer |
| 2009/0216084 A1 | 8/2009 | Yamane |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0280322 A1* | 11/2010 | Mizuyoshi ........... A61B 1/0638 600/178 |
| 2010/0296178 A1 | 11/2010 | Genet |
| 2011/0034769 A1 | 2/2011 | Adair |
| 2011/0063427 A1 | 3/2011 | Fengler |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takato |
| 2011/0263938 A1 | 10/2011 | Levy |
| 2011/0282144 A1 | 11/2011 | Gettman |
| 2011/0292258 A1 | 12/2011 | Adler |
| 2012/0040305 A1 | 2/2012 | Karazivan |

(56) References Cited

U.S. PATENT DOCUMENTS

| | | |
|---|---|---|
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |
| 2012/0253121 A1 | 10/2012 | Kitano |
| 2012/0277535 A1 | 11/2012 | Hoshino |
| 2012/0300999 A1 | 11/2012 | Bayer |
| 2013/0053646 A1* | 2/2013 | Yamamoto ............ A61B 1/043 600/180 |
| 2013/0057724 A1 | 3/2013 | Miyahara |
| 2013/0066297 A1 | 3/2013 | Shtul |
| 2013/0085329 A1 | 4/2013 | Morrissette |
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0150671 A1 | 6/2013 | Levy |
| 2013/0169843 A1 | 7/2013 | Ono |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0222640 A1 | 8/2013 | Baek |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0148644 A1 | 5/2014 | Levi |
| 2014/0213850 A1 | 7/2014 | Levy |
| 2014/0225998 A1 | 8/2014 | Dai |
| 2014/0276207 A1* | 9/2014 | Ouyang ............ A61B 1/00066 600/567 |
| 2014/0296628 A1 | 10/2014 | Kirma |
| 2014/0296643 A1 | 10/2014 | Levy |
| 2014/0296866 A1 | 10/2014 | Salman |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1* | 8/2015 | Cline ............ A61B 1/043 600/109 |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| EP | 1690497 | 8/2006 |
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | H1043129 | 2/1998 |
| JP | H10239740 | 9/1998 |
| JP | 11137512 | 5/1999 |
| JP | 2005253543 | 9/2005 |
| JP | 2006025888 | 2/2006 |
| JP | 2006068109 | 3/2006 |
| JP | 2010178766 A | 8/2010 |

(56) References Cited

FOREIGN PATENT DOCUMENTS

| | | |
|---|---|---|
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 | 12/2010 |
| WO | 2012038958 | 3/2012 |
| WO | 2012056453 | 5/2012 |
| WO | 2012075153 A2 | 6/2012 |
| WO | 2012077116 | 6/2012 |
| WO | 2012077117 | 6/2012 |
| WO | 2012096102 | 7/2012 |
| WO | 2012120507 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

International Search Report for PCT/US14/37004, Sep. 25, 2014.
International Search Report for PCT/US14/38094, Nov. 6, 2014.
International Search Report for PCT/US2015/012751, mailed on Jun. 26, 2015.
International Search Report for PCT/US2014/58143, mailed on Jan. 21, 2015.
International Search Report for PCT/US2014/071085, mailed on Mar. 27, 2015.
International Search Report for PCT/US2015/027902, mailed on Jul. 23, 2015.
International Search Report for PCT/US2015/012506, mailed on Dec. 11, 2015.
International Search Report for PCT/US2015/29421, mailed on Aug. 7, 2015.
International Search Report for PCT/US2015/28962, mailed on Jul. 28, 2015.
International Search Report for PCT/US2015/47334, mailed on Dec. 28, 2015.
International Search Report for PCT/US2015/41396, mailed on Sep. 29, 2015.
International Search Report for PCT/US2015/66486, mailed on Dec. 17, 2015.
International Search Report for PCT/US2015/6548, mailed on Feb. 26, 2016.
Office Action dated Feb. 4, 2016 for U.S. Appl. No. 14/271,234.
Corrected Notice of Allowance dated Apr. 13, 2016 for U.S. Appl. No. 13/680,646.
Notice of Allowance dated Mar. 28, 2016 for U.S. Appl. No. 13/413,059.
Notice of Allowance dated Mar. 29, 2016 for U.S. Appl. No. 13/680,646.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.

* cited by examiner

ENDOSCOPE TIP POSITION VISUAL INDICATOR AND HEAT MANAGEMENT SYSTEM

CROSS-REFERENCE TO RELATED APPLICATIONS

The present specification relies on, for priority, U.S. Provisional Patent Application No. 61/822,805, entitled "Method and System for Providing An Endoscope Visual Tip Indicator", and filed on May 13, 2013.

The present specification is also a continuation-in-part application of U.S. patent application Ser. No. 13/984,028, entitled "Multi-Element Cover for a Multi-Camera Endoscope" and filed on Aug. 22, 2013, which is a 371 National Stage Entry of PCT Application Number PCT/IL2012/050037, of the same title and filed on Feb. 6, 2012, which, in turn, relies upon U.S. Provisional Patent Application No. 61/439,948, filed on Feb. 7, 2011, for priority, and is herein incorporated by reference.

The present specification is also a continuation-in-part application of U.S. patent application Ser. No. 13/992,021, entitled "Fluid Channeling Component of a Multi-Camera Endoscope" and filed on Jun. 6, 2013, which is a 371 National Stage Entry of PCT Application Number PCT/IL2011/050050, entitled "Flexible Electronic Circuit Board Multi-Camera Endoscope" and filed on Dec. 8, 2011, which, in turn, relies upon U.S. Provisional Patent Application No. 61/421,240, filed on Dec. 9, 2010, for priority, and is herein incorporated by reference.

The present specification is also a continuation-in-part application of U.S. patent application Ser. No. 13/992,014, entitled "Flexible Electronic Circuit Board for a Multi-Camera Endoscope" and filed on Jun. 6, 2013, which is a 371 National Stage Entry of PCT Application Number PCT/IL2011/050049, of the same title and filed on Dec. 8, 2011, which, in turn, relies upon U.S. Provisional Patent Application No. 61/421,238, filed on Dec. 9, 2010, for priority, and is herein incorporated by reference.

The present specification is also a continuation-in-part application of U.S. patent application Ser. No. 13/882,004, entitled "Optical Systems for Multi-Sensor Endoscopes" and filed on May 23, 2013, which is a 371 National Stage Entry of PCT Application Number PCT/IL2011/000832, of the same title and filed on Oct. 27, 2011, which, in turn, relies upon U.S. Provisional Patent Application No. 61/407,495, filed on Oct. 28, 2010, for priority, and is herein incorporated by reference.

The present specification is also a continuation-in-part application of U.S. patent application Ser. No. 13/822,908, entitled "Multi-Camera Endoscope Having Fluid Channels" and filed on Mar. 13, 2013, which is a 371 National Stage Entry of PCT Application Number PCT/IL2011/000745, of the same title and filed on Sep. 20, 2011, which, in turn, relies upon U.S. Provisional Patent Application No. 61/384,354, filed on Sep. 20, 2010, for priority, and is herein incorporated by reference.

The present specification is also a continuation-in-part application of U.S. patent application Ser. No. 13/713,449, entitled "Removable Tip Endoscope" and filed on Dec. 13, 2012, which, in turn, relies upon U.S. Provisional Patent Application No. 61/569,796, of the same title and filed on Dec. 13, 2011, for priority, and is herein incorporated by reference.

The present application is also a continuation-in-part application of the following United States patent applications, which are herein incorporated by reference in their entirety:

U.S. patent application Ser. No. 13/655,120, entitled "Multi-Camera Endoscope" and filed on Oct. 18, 2012;

U.S. patent application Ser. No. 13/212,627, entitled "Multi-Viewing Element Endoscope" and filed on Aug. 18, 2011; and U.S. patent application Ser. No. 13/190,968, entitled "Multi-Camera Endoscope" and filed on Jul. 26, 2011, all of which are continuation-in-part applications of U.S. patent application Ser. No. 13/119,032, entitled "Multi-Camera Endoscope" and filed on Jul. 15, 2011, which is a 371 National Stage Entry of PCT Application Number PCT/IL2010/000476, of the same title and filed on Jun. 16, 2010, which, in turn, relies upon U.S. Provisional Patent Application No. 61/218,085, for priority.

The present specification is also a continuation-in-part application of U.S. patent application Ser. No. 13/413,252, entitled "Multi Camera Endoscope Assembly Having Multiple Working Channels" and filed on Mar. 6, 2012, which, in turn, relies upon U.S. Provisional Patent Application No. 61/449,746, of the same title and filed on Mar. 7, 2011, for priority, and is herein incorporated by reference.

The present specification is also a continuation-in-part application of U.S. patent application Ser. No. 13/413,141, entitled "Multi Camera Endoscope Having a Side Service Channel" and filed on Mar. 6, 2012, which, in turn, relies upon U.S. Provisional Patent Application No. 61/449,743, of the same title and filed on Mar. 7, 2011, for priority, and is herein incorporated by reference.

The present specification is also a continuation-in-part application of U.S. patent application Ser. No. 13/413,059, entitled "Endoscope Circuit Board Assembly" and filed on Mar. 6, 2012, which, in turn, relies upon U.S. Provisional Patent Application No. 61/449,741, of the same title and filed on Mar. 7, 2011, for priority, and is herein incorporated by reference.

The present specification is also a continuation-in-part application of U.S. patent application Ser. No. 13/412,974, entitled "Camera Assembly for Medical Probes" and filed on Mar. 6, 2012, which, in turn, relies upon U.S. Provisional Patent Application No. 61/449,739, of the same title and filed on Mar. 7, 2011, for priority, and is herein incorporated by reference.

All of the above-mentioned applications are herein incorporated by reference in their entirety.

FIELD

The present invention relates generally to an endoscope with a plurality of discrete illuminators for illuminating fields of view of one or more of the endoscope's viewing elements, and more specifically, to methods and systems for managing the amount of heat generated by discrete illuminators in an endoscope tip and enable such illuminators to be viewed outside a patient's body when the tip is inside the patient's body.

BACKGROUND

An endoscope is a medical instrument used for examining and treating internal body parts such as the alimentary canals, airways, the gastrointestinal system, and other organ systems. Conventional endoscopes have a flexible tube carrying a fiber optic light guide for directing light from an external light source situated at a proximal end of the tube to a distal tip. Also, most endoscopes are provided with a channel, through which medical devices, such as forceps, probes, and other tools, may be passed. Further, during an endoscopic procedure, fluids, such as water, saline, drugs, contrast material, dyes, or emulsifiers are often introduced or evacuated via the flexible tube. A plurality of channels, one each for introduction and suctioning of liquids, may be provided within the flexible tube.

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy among others. Endoscopes may be inserted into the body's natural orifices or through an incision in the skin.

Endoscopes, such as colonoscopes, that are currently being used, typically have a front camera for viewing the internal organ, such as the colon, an illuminator for illuminating the field of view of the camera, a fluid injector for cleaning the camera lens and sometimes also the illuminator and a working channel for insertion of surgical tools, for example, for removing polyps found in the colon. The illuminators commonly used are fiber optics which transmit light, generated remotely, to the endoscope tip section.

In more currently developed endoscopes, discrete illuminators, such as light-emitting diodes (LEDs), have been incorporated in an endoscope tip for providing illumination.

While discrete illuminators, such as LEDs, provide the illumination required for enabling operation of the endoscope, they also produce heat during their operation. The heat produced may harm the internal organs of a patient being operated upon. Hence, there is need for a system and method of operating the LEDs so that a minimal amount of heat is produced while still obtaining a threshold level of illumination. There is also a need for providing a temperature modulated endoscope tip visual indicator.

Additionally, navigating an endoscope through a patient's body can be confusing and is made challenging by virtue of not knowing precisely where the tip of the endoscope may be located at any given point in time. Accordingly, there is a need for endoscopic system that can provide a physician with an indication of where the endoscope tip may be located in a patient during a procedure.

SUMMARY

In an embodiment, the present specification is directed toward a system for managing heat generated in a tip of an endoscope, comprising: a controller external to the endoscope, wherein said controller comprises a memory for storing programmatic functions and a processor for executing said programmatic functions; an input device in data communication with said controller, wherein said input device is adapted to receive data indicative of a programmatic function and wherein said input device is configured to communicate said data indicative of a programmatic function to the controller; and a plurality of discrete illuminators positioned within said tip and in electrical communication with said controller, wherein each of said plurality of discrete illuminators emits an amount of visible light and wherein said controller executes a programmatic function based upon said data indicative of a programmatic function that causes at least one of said plurality of discrete illuminators to modulate an amount of visible light emitted by it in accordance with said programmatic function.

In another embodiment, the present specification is directed toward a method of tracking a position of an endoscope tip within a human body, comprising one or more viewing elements and one or more discrete illuminators for illuminating fields of view of the viewing elements, wherein each viewing element is associated with at least one discrete illuminator, the method comprising: providing a controller external to the endoscope, wherein said controller comprises a memory for storing programmatic functions and a processor for executing said programmatic functions; providing an input device in data communication with said controller, wherein said input device is adapted to receive data indicative of a programmatic function and wherein said input device is configured to communicate said data indicative of a programmatic function to the controller; and providing a plurality of discrete illuminators positioned within said tip and in electrical communication with said controller, wherein each of said plurality of discrete illuminators emits an amount of visible light and wherein said controller executes a programmatic function based upon said data indicative of a programmatic function that causes at least one of said plurality of discrete illuminators to modulate an amount of visible light emitted by it in accordance with said programmatic function.

Optionally, the discrete illuminators emit a light intensity of 28 lumens per second while the system is not operating in flash/intermittent mode. In one embodiment, this is defined as the baseline operational intensity.

Optionally, the programmatic function defines, for at least one of said plurality of discrete illuminators, a first non-zero power level for a first period of time and a second non-zero power level for a second period of time.

Optionally, the first power level causes at least one of said plurality of discrete illuminators to emit an amount of visible light in a range of greater than 40 lumens. Still optionally, the second power level causes at least one of said plurality of discrete illuminators to emit an amount of visible light in a range less than 40 lumens.

In an embodiment, the programmatic function may define a duty cycle for at least one of said plurality of discrete illuminators, and, wherein during 30% of said duty cycle, the programmatic function defines a first lumen level that is greater than 40 lumens. Optionally, during 70% of said duty cycle, the programmatic function defines a second lumen level that is less than 40 lumens.

Optionally, the input device is at least one of a touch screen display, a button on a handle of the endoscope, a keypad, or a mobile device.

In one embodiment, the programmatic function may define, for at least one of said plurality of discrete illuminators, a first power level that causes at least one of said plurality of discrete illuminators to emit an amount of visible light in a range of 45-55 lumens for a first period of time and a second power level that causes the at least one of said plurality of discrete illuminators to emit an amount of visible light in a range of 15-25 lumens for a second period of time.

In another embodiment, the programmatic function may define, for at least one of said plurality of discrete illuminators, a constant power level that causes the at least one of said plurality of discrete illuminators to emit an amount of visible light in a range of 20-35 lumens for a second period of time.

Optionally, one or more discrete illuminator are operated to emit light having an intensity of at least 15 lumens for a maximum of 60 milliamperes current for a duration of 3 to 15 seconds with pulses of 10 to 50 milliseconds in duty cycle ranging between 10% to 50%.

Optionally, the same programmatic function is applied to the plurality of discrete illuminators located within the endoscope tip.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION

In one embodiment, the present specification discloses an endoscope having a tip section equipped with multiple viewing elements. In one embodiment, three viewing elements, typically comprising lens assemblies such as a camera and/or a fiber optic lens assembly and image sensors, are employed, to deliver a display comprising three parts. In an embodiment, each of the viewing elements' field of view is illuminated by a discrete illuminator, such as a LED, that is operated in a flash mode for reducing the amount of heat produced while maintaining a threshold level of illumination. The flash mode of operation of the LEDs enables a physician to obtain a position of the endoscope tip within a patient's body from outside by viewing the light emitted by the LEDs. Since the light is emitted for short pre-defined periods of time, the heat generated by the LEDs during their respective periods of operation is within a safe threshold value, and does not cause any burn injury inside the patient's body and within the lumen under inspection.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
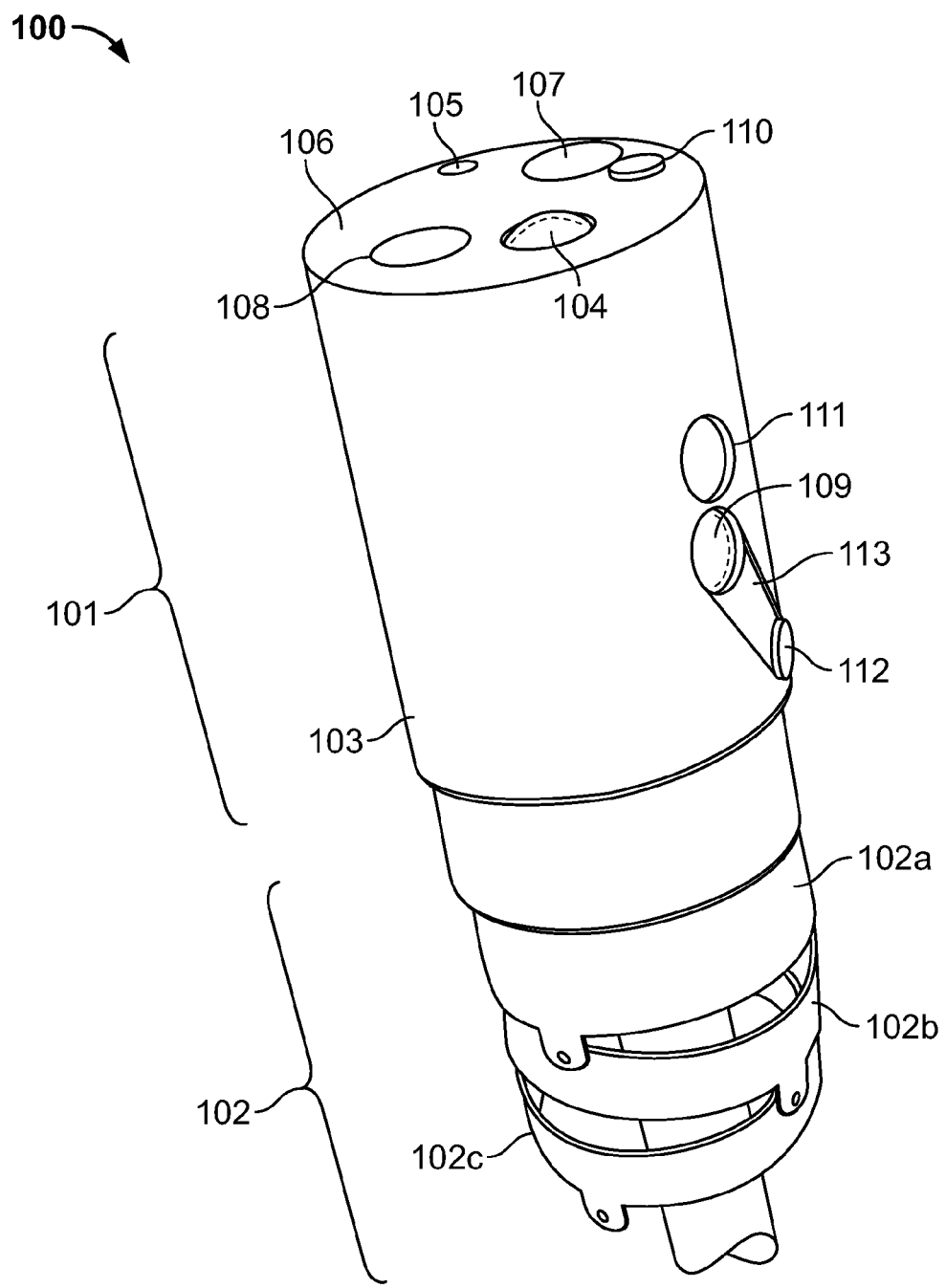
FIG. 1 illustrates a perspective view of a multi-viewing element endoscope, in accordance with one embodiment.

Referring to FIG. 1, a perspective view of a multi-viewing element endoscope 100 is shown in detail, in accordance with an embodiment of the present specification. As shown in FIG. 1, endoscope 100 includes an elongated shaft (not shown), a bending section (partially shown) 102 and a tip section 101 which terminates the endoscope. Bending section 102, in one embodiment, comprises moveably attached vertebrae sections 102a, 102b, and 102c for flexible movement of the endoscope within a patient's lumen. Tip section 101 of the endoscope 100 includes therein a front-pointing viewing element 104 which captures images through a window in a distal end surface 106 of the tip section.

In an embodiment, a discrete front illuminator 108, which is, in an embodiment, a light-emitting diode (LED), is associated with front-pointing viewing element 104 and is used for illuminating its field of view through an opening in distal end surface 106. In various embodiments of the present specification, different types of LEDs are used, such as, but not limited to, a white light LED, an infrared light LED, a near infrared light LED or an ultraviolet light LED. The term "discrete", in regard to front illuminator 108, refers to an illumination source which generates light internally within the tip or distal end of the endoscope, in contrast to a non-discrete illuminator which may be, for example, a fiber optic channel that transmits light generated remote from the tip. In a different configuration (not shown), two or more discrete front illuminators are present in the tip section, such as for supplying overall stronger illumination and/or for increasing the angular coverage of the illumination. In one embodiment, these two or more discrete front illuminators are located next to one another so that they share a same protective window on the distal end surface of the tip section.

During procedures, a physician may want to visually determine the progression of the endoscope tip through a patient's body. In one embodiment, the endoscope system enables a physician to see the movement of the distal tip of the endoscope tip within a patient's body from the outside, through the patient's skin, using a high level of illumination generated by the discrete illuminators which, in one embodiment, are LEDs. However, the higher the illumination level, the more heat that is consequently generated. In order to lower the amount of heat generated, in one embodiment, the LEDs are operated in accordance with a predefined frequency, i.e. using flashes or intermittent operation, to generate light which is visible from outside the patient's body, but in a manner that decreases the total amount of heat generated. In this mode of operation, the LEDs emit light of predefined intensities for predetermined periods of time. As the light is emitted for short pre-defined periods of time, the heat generated by the LEDs during their periods of operation is within a safe threshold value, and does not cause any burning of patient tissue.

In order to see the movement of the distal tip of the endoscope through the patient's skin, the LEDs must emit a threshold level of illumination. In an embodiment, during flash mode of operation, the discrete illuminators continuously emit light for a duration of less than 10 seconds. In one embodiment, the discrete illuminators continuously emit light for a duration of approximately 7 seconds. In an embodiment, a duty cycle of 30% is employed when operating in flash mode. A duty cycle is defined as the percentage of one period in which a signal is active; a period is the time it takes for a signal to complete an on-and-off cycle. In other embodiments, other values of duty cycles are also employed. In another embodiment, the amount of light emitted is approximately 51 lumens per second for approximately 30% of the total time during which the system is operating in flash mode and approximately 21 lumens per second for remaining 70% of the total time during which the system is operating in flash mode. In one embodiment, the amount of light emitted while the system is not operating in flash mode is 28 lumens per second. In conventional endoscopes, a light of 28 lumens per second of intensity is generated constantly during procedures and, thus, this is the baseline operational intensity.

In an embodiment, the discrete illuminators are operated to emit non-steady intensities of light.

In an embodiment, each discrete illuminator is operated to emit light with an intensity of at least 15 lumens and with a maximum current of 60 milliamperes for a duration (period) ranging from 3 to 15 seconds with a pulse duration of 10 to 50 milliseconds in a duty cycle ranging between 10% to 50%.

In an embodiment, the illumination provided by the LEDs is uniform around all sides of the tip of an endoscope. This makes it easy to know which side of the tip, inside a patient's body cavity, is facing outward from within the patient, as such can be seen from the outside of the body. In an embodiment, the flash mode of operation of the LEDs for providing illumination is controlled by a controller unit such as is described in conjunction with FIG. 4 and described in detail below. In another embodiment, the flash mode of operation of the LEDs for providing illumination is controlled manually by the person operating the endoscope. For example, in an embodiment, the endoscope has a button on the handle which, when pressed, activates the LED to cycle through different operational modes. In an embodiment, a first press causes the LEDs to remain on constantly. In an embodiment, a second press activates the LEDs to flash on and off. In an embodiment, a third press causes the LEDs to change from a first high intensity level to a second low intensity level. It should be noted herein that any combination of such controls is within the scope of this application.

Referring back to FIG. 1, in an embodiment, a front fluid injector 110 is used for cleaning at least one of front-pointing viewing element 104 and discrete front illuminator 108. In an embodiment, the distal end surface 106 includes a hole defining a working channel 107, which, in an embodiment, is coupled with a hollow tube configured for insertion of surgical tools to operate on various tissues. In an embodiment, a pathway fluid injector 105, defined by another hole in distal end surface 106, is used for inflating and/or cleaning the body cavity into which endoscope 100 is inserted.

In an embodiment, the tip section 101 may further include therein a side-pointing viewing element 109 which captures images through a hole in a cylindrical surface 103 of the tip section. In an embodiment, a discrete side illuminator 111, which is optionally similar to discrete front illuminator 108, is associated with side-pointing viewing element 109 and is used for illuminating its field of view through another hole in cylindrical surface 103. In another configuration, two or more discrete side illuminators are present in the tip section, such as for supplying overall stronger illumination and/or for increasing the angular coverage of the illumination. In one embodiment, these two or more discrete side illuminators are located next to one another so that they share a same protective window on the cylindrical surface of the tip section.

In an embodiment, a side fluid injector 112 is used for cleaning at least one of side-pointing viewing element 109 and discrete side illuminator 111. In order to prevent tissue damage when cylindrical surface 103 of tip section 104 contacts a side wall of the body cavity, in an embodiment, the side fluid injector 112 and side-pointing viewing element 109 are located in a depression 113 in the cylindrical surface. In an alternative configuration, one or more discrete side illuminators are also included in the depression, so that fluid injected from the side fluid injector can reach them. In yet another alternative configuration, a side-pointing viewing element, one or more side illuminators and a side fluid injector are positioned on essentially the same level as the cylindrical surface of the tip section and thus, are not located in a depression.

In some embodiments, at least one of said discrete front and side illuminators is configured to emit white light. In some embodiments, at least one of said discrete front and side illuminators is configured to emit ultraviolet light. In some embodiments, at least one of said discrete front and side illuminators is configured to emit infrared light. In some embodiments, at least one of said discrete front and side illuminators is configured to emit near-infrared light. In some embodiments, said discrete front and side illuminators are configured to emit light in different wavelengths. In some embodiments, said tip section further comprises an additional discrete front illuminator configured to emit light having a different wavelength than said discrete front illuminator. In some embodiments, said additional discrete front illuminator and said discrete front illuminator are configured to simultaneously emit light, each at a different wavelength. In some embodiments, said tip section further comprises an additional discrete side illuminator configured to emit light having a different wavelength than said discrete side illuminator. In some embodiments, said additional discrete side illuminator and said discrete side illuminator are configured to simultaneously emit light, each at a different wavelength.

It should be appreciated that the number of front illuminators can be 1, 2, 3, 4 or more. A front illuminator is positioned on the planar surface defining the distal end of the tip. It should also be appreciated that the number of side illuminators on one side of the tip can be 1, 2, 3, 4 or more and on the opposing side of the tip can also be can be 1, 2, 3, 4 or more. Side illuminators are positioned in depressions positioned on the cylindrical surfaces defining the circumference of the tip.

Figure 2:
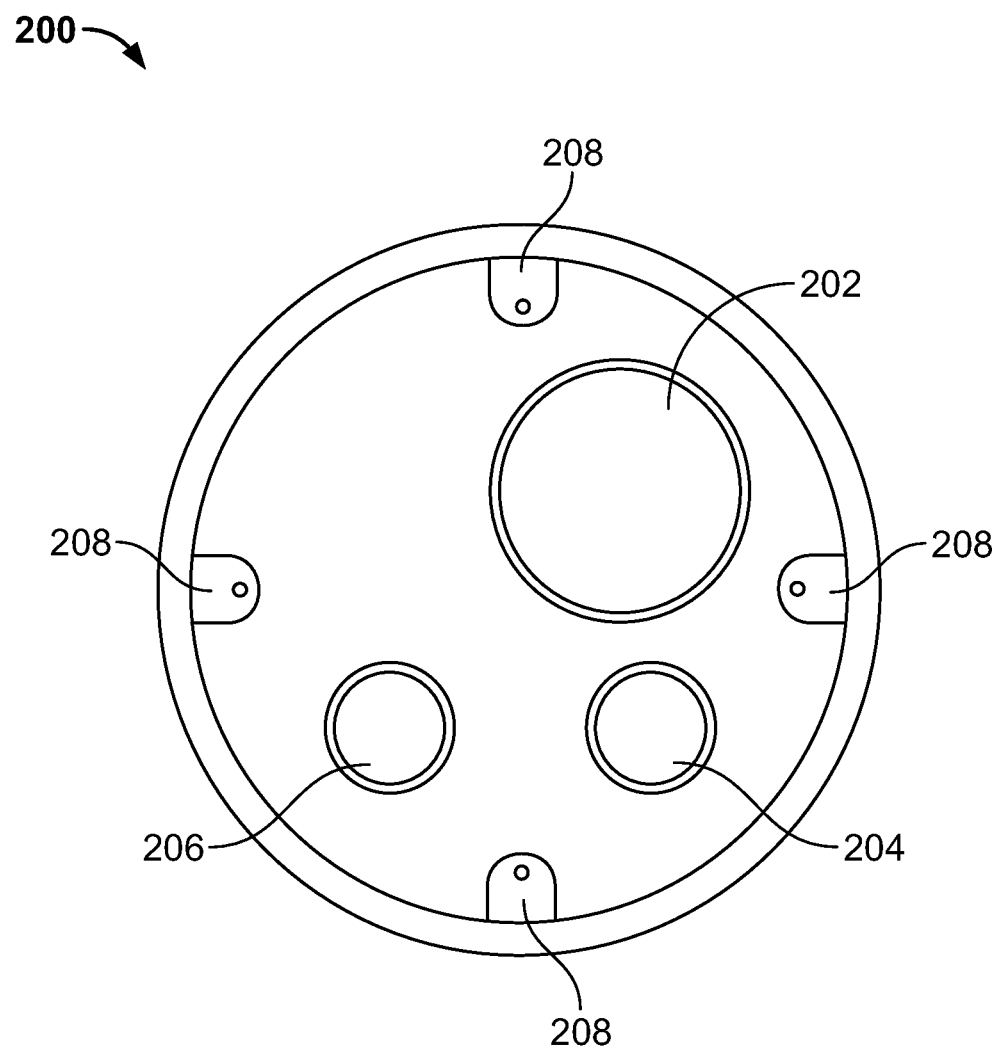
FIG. 2 illustrates a cross-sectional view of a bending section of a multi-viewing element endoscope, in accordance with one embodiment.

Reference is now made to FIG. 2, which shows a cross-sectional view of a bending section 200 of a multi-viewing element endoscope, such as multi-viewing element endoscope 100 of FIG. 1. A plurality of steering cable guides/eyes, such as four guides 208, are positioned on the internal walls of bending section 200. Steering cables are threaded through guides 208 to enable the maneuvering of bending section 200. In an embodiment, the bending section 200 also includes a working channel 202, through which surgical tools can be inserted, a fluid channel 206, through which fluids and/or liquids can be infused, and an electrical channel 204, through which a plurality of electrical cables are threaded, for transmitting video signals from the cameras and for supplying power to the viewing elements and the discrete illuminators. In some embodiments, each of said discrete front and side illuminators comprises one or more light-emitting diodes (LED).

Figure 3:
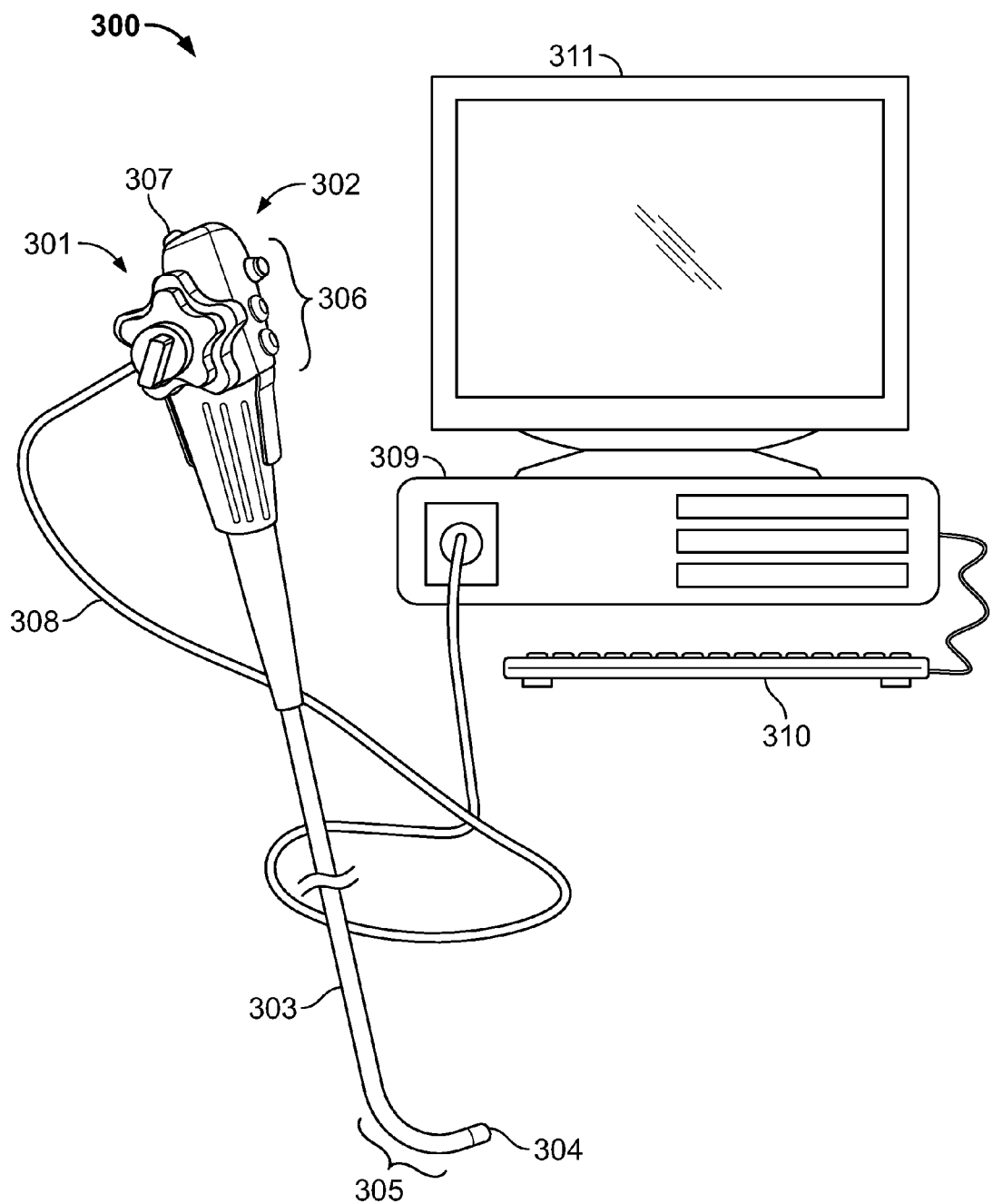
FIG. 3 illustrates a multi-viewing element endoscopy system, in accordance with one embodiment.

Reference is now made to FIG. 3, which shows a multi-viewing element endoscopy system 300. System 300 includes a multi-viewing element endoscope 301. Multi-viewing element endoscope 301 includes a handle 302, from which an elongated shaft 303 emerges. Elongated shaft 303 terminates with a tip section 304 which is turnable by way of a bending section 305. Handle 302 is used for maneuvering elongated shaft 303 within a body cavity. In an embodiment, the handle includes one or more buttons and/or knobs and/or switches 306 which control bending section 305 as well as functions such as the flash mode, fluid injection and suction. In an embodiment, handle 302 further includes a working channel opening 307 through which surgical tools can be inserted.

A utility cable 308 connects between handle 302 and a controller 309. Utility cable 308 includes therein one or more fluid channels and one or more electrical channels. In an embodiment, the electrical channel(s) includes at least one data cable for receiving video signals from the front and side-pointing viewing elements, as well as at least one power cable for providing electrical power to the viewing elements and to the discrete illuminators.

In an embodiment, the controller 309 governs power transmission to the endoscope 301 tip section 304, such as for the tip section's cameras and illuminators. In an embodiment, controller 309 controls the operation of the discrete illuminators. In one embodiment, controller 309 further controls one or more fluid, liquid and/or suction pumps which supply corresponding functionalities to endoscope 301. In one other embodiment, one or more input devices, such as a keyboard 310 or touchscreen (not shown), are connected to controller 309 for the purpose of human interaction with the controller. In another configuration (not shown), an input device, such as a keyboard, is integrated with the controller in a same casing.

In one embodiment, a display 311 is connected to controller 309, and is configured to display images and/or video streams received from the viewing elements of multi-viewing element endoscope 301. In some embodiments, display 311 has more than one display unit. In an embodiment, the display 311 further provides the means to display a touch screen user interface for allowing a human operator to set various features of system 300. In an embodiment, a human operator uses the user interface to input predefined time intervals for which the LEDs provide illumination.

Figure 4:
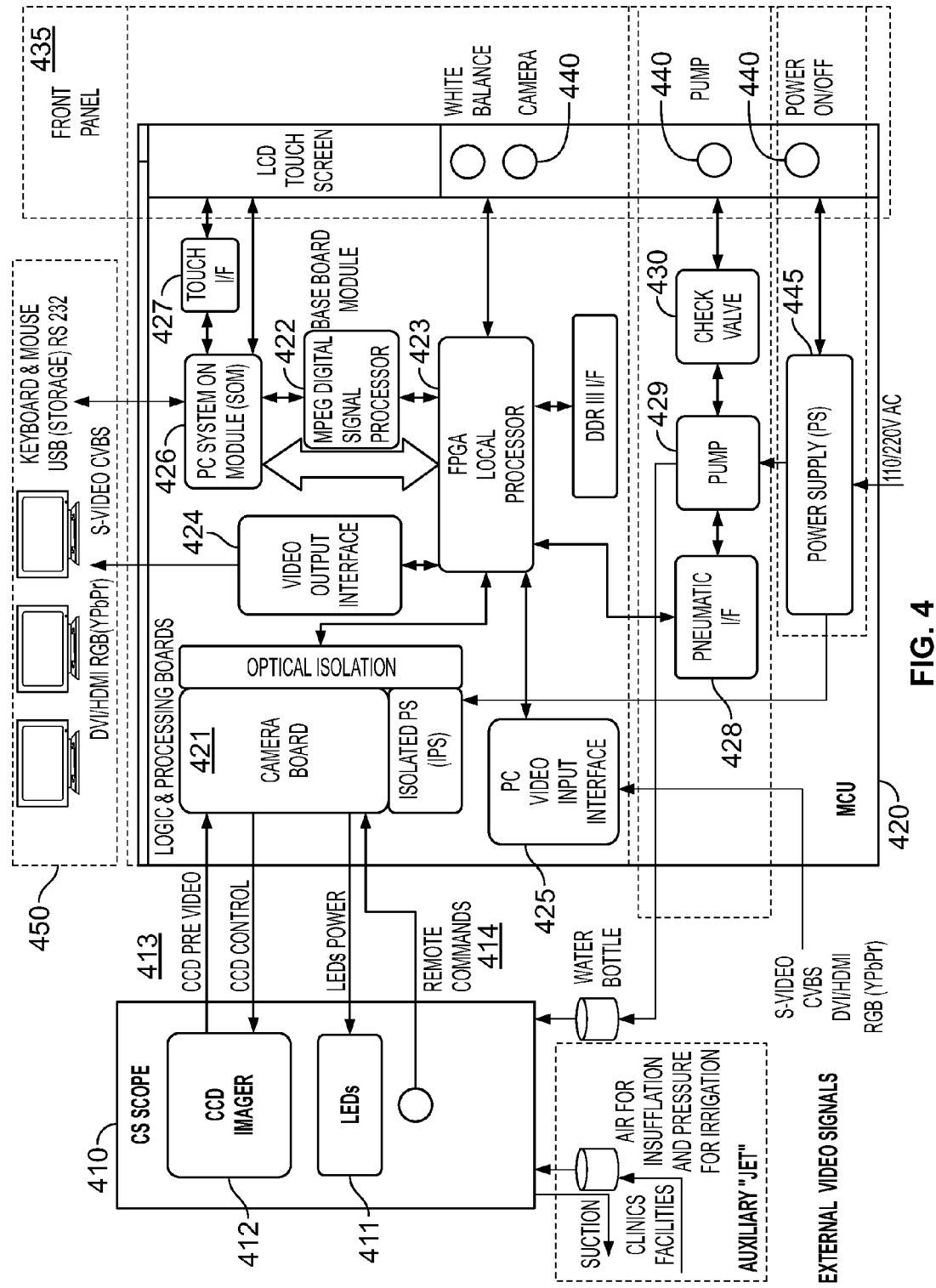
FIG. 4 is a block diagram illustrating overall video processing architecture of a multi-viewing element endoscopy system, in accordance with one embodiment.

Reference is now made to FIG. 4, which is a block diagram illustrating overall video processing architecture, in accordance with an embodiment of the present specification. FIG. 4 details the operational connection between video processing controller 420, endoscope 410 and the display units 450. The video processing controller 420 controls the flash mode of operation of the LEDs. In an embodiment, a predefined period of time for which the LEDs are required to provide continuous illumination is stored in a memory of the video processing controller 420. Also, in an embodiment, one or more values of illumination intensities along with corresponding durations of illumination is pre-defined in the video processing controller 420. Video processing controller 420 further comprises a camera board 421 that transmits appropriate commands to control the power supply to the LEDs 411 and to control the operation of CCD imager 412 (comprising one or more viewing elements and image sensors) in the endoscope. The camera board, in turn, receives video signal 413 generated by the CCD imager and also other remote commands 414 from the endoscope.

Video processing controller 420 further comprises elements for processing the video obtained from the imager 412, including MPEG Digital Signal Processor 422 and FPGA local processor 423. The FPGA 423 is responsible for video interpolation and on-screen display overlay prior to sending the video to the MPEG DSP 422. The FPGA 423 acts as a main controller of the system for image processing, video writing and on-screen display. The video signal is sent for display through Video output interface 424. A video input interface 425 is also provided for receiving video input from an external video source.

System-On-Module (SOM) 426 provides an interface to input devices such as keyboard and mouse, while Touch I/F 424 provides a touchscreen interface. In an embodiment, the controller 420 further controls one or more fluid, liquid and/or suction pump(s) which supply corresponding functionalities to the endoscope through pneumatic I/F 428, pump 429 and check valve 430. The controller further comprises a power supply on board 445 and a front panel 435 which provides operational buttons 440 for the user.

Figure 5:
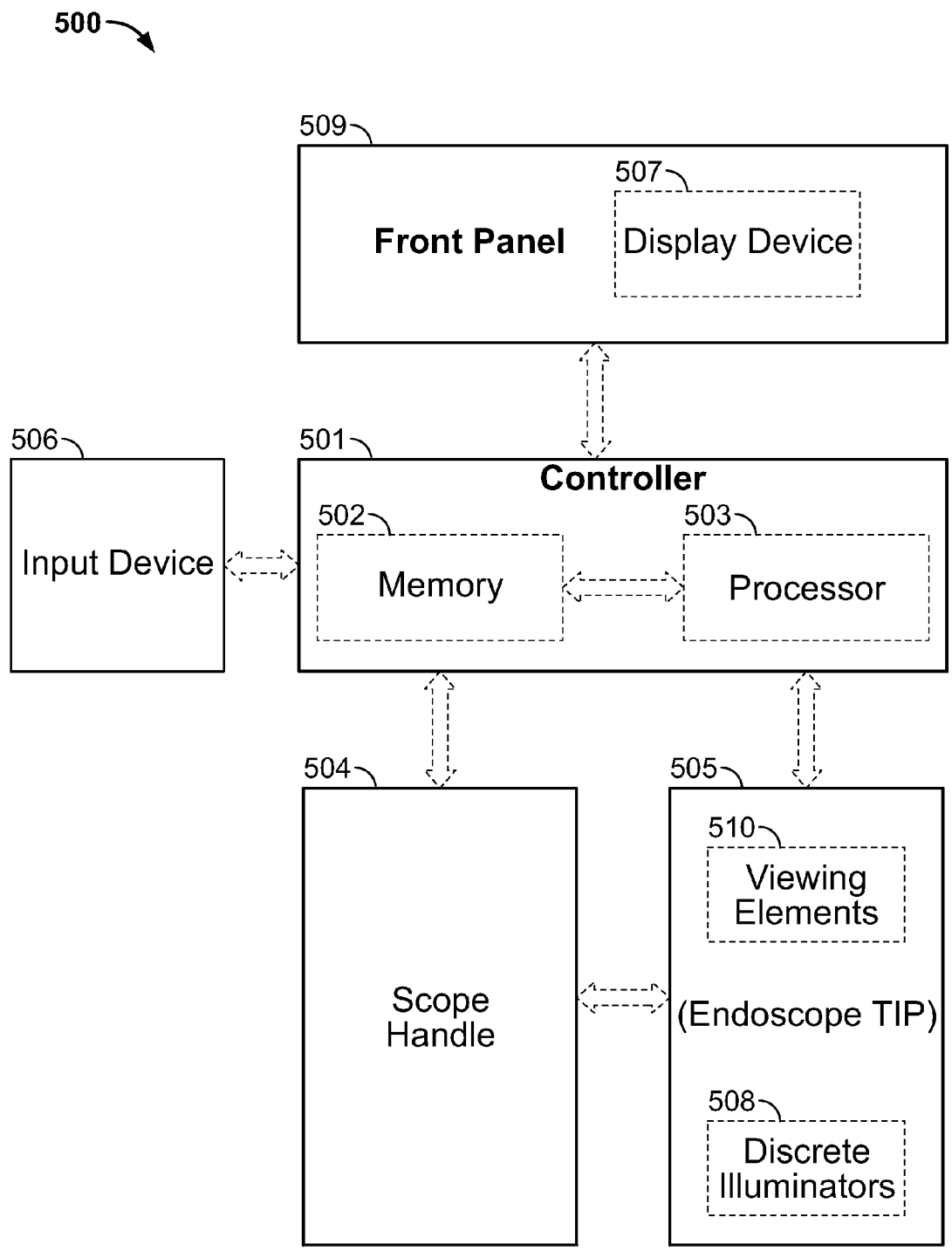
FIG. 5 illustrates a block diagram showing the data communication between various components of the endoscopy system, in accordance with one embodiment.

FIG. 5 is a block diagram describing the data communication between various components of the endoscopy system in accordance with an embodiment of the present specification. As shown in FIG. 5, the endoscopy system 500 comprises an external controller 501 which, in an embodiment, provides the controls required for displaying images or video of internal organs captured by the endoscope on a display device. In an embodiment, the controller 501 governs power transmission to the endoscope's tip section, such as for the tip section's viewing elements and illuminators. In an embodiment, one or more input devices 506, such as, but not limited to, a keyboard, a touch screen, and at least one display may be connected to controller 501. In an embodiment, the controller 501 also comprises a front panel 509 having a display screen 507 for displaying operational information concerning an endoscopy procedure when the endoscope is in use. In an embodiment, the display screen 507 is configured to display images and/or video streams received from the viewing elements of the multi-viewing element endoscope. In an embodiment, display screen 507 is a touch screen device.

In an embodiment, the controller 501 comprises a memory module 502 for storing information and a processor 503 for executing various computer programmed commands fed to the system. In an embodiment, the endoscopy system 500 comprises a handle 504 which contains the means through which a physician can perform the procedure and control various functionalities of the endoscopy system 500. As shown in FIG. 5, the handle 504 and the controller 501 are in data communication with the endoscope tip section 505, which in an embodiment, contains a plurality of discrete illuminators 508 that illuminate the fields of view of one or more viewing elements 510 located on the endoscope tip section 505. In an embodiment, the plurality of discrete illuminators 508 comprises one or more different types of LEDs.

In an embodiment of the present specification, in response to an input from either the input device 506 (such as, but not limited to, display screen 507 located on front panel 509 of the external controller) or the handle 504, the controller 501 modulates the power level and the resulting illumination intensity, and thus, the brightness of discrete illuminators 508. In one embodiment, it is possible to modulate the illumination intensity and power level of the discrete illuminators so that the light emitted by one or more illuminators 508 is sufficiently bright and is visible outside the patient's body which helps in locating the position of endoscope tip within the body. In an embodiment, the controller modulates the power levels of one or more illuminators 508 such that the total heat generated during the process is within a threshold limit that may be pre-defined.

In one embodiment, the controller 501 modulates the power level of a first set of illuminators 508 and operates the first set of illuminators at a higher intensity for a specific duration of time such that the light emitted by them is visible outside the patient body and at the same time, to compensate for the excess heat generated due to higher intensity of these illuminators, the controller 501 also modulates the power level of a second set of illuminators 508 and operates the second set of illuminators at a lower intensity for a specific duration of time.

In one embodiment, the controller 501 modulates the power level and resulting illumination intensity of one or more discrete illuminators 508 and operates them in a flash/intermittent mode wherein the resulting illumination intensity fluctuates across a set of one or more intensity levels for a pre-defined period of time and once that time period is over, it again modulates the power levels of these illuminators to bring the illuminators to original levels corresponding to a baseline operational intensity. In an embodiment, the total period of flash mode of operation, the set of intensity levels and corresponding time periods in each clock cycle are chosen such that during the flash mode of operation, the emitted light is visible outside the patient body while at the same time total heat produced by the system is within a threshold limit that may be pre-defined.

In one embodiment, the controller 501 is in independent data communication with each of the discrete illuminators 508 and controls the flash mode of operation of these illuminators by separately modulating the power transmitted to each of the illuminators 508.

In one embodiment, in response to an input, the controller modulates the power level of one or more illuminators 508 to change the intensity, and therefore, the brightness of the illuminators in accordance with a predefined function. In one embodiment, the predefined function includes parameters, such as, but not limited to 1) a plurality of power levels that can be applied to at least one illuminator and 2) the amount of time that is spent at each power level. In an embodiment, based on input instructions, the controller 501 applies the same predefined function to each discrete illuminator. In one embodiment, the same predefined function is applied to each discrete illuminator with different parameter values. In an embodiment, multiple predefined functions are stored in the memory 502 and based on the requirement or user instructions, one or more of these functions are applied to one or more discrete illuminators 508.

In an embodiment, the controller 501 operates one or more discrete illuminators 508 in the flash/intermittent mode while the physician presses a designated button on handle 504. Once the physician locates the position of endoscope tip and subsequently releases the button on handle 504, the controller 501 modulates the power level of illuminators 508 and brings the illuminators back to baseline operational intensity levels.

In one embodiment, the user can locate the position of endoscope tip from a specific direction by directing the controller to operate the illuminators that are located in that direction in a flash/intermittent mode.

In an embodiment, the system enables the user, via the appropriate controller and predefined functions, to increase or decrease the level of intensity used in the flash/intermittent mode based on the user's requirements. In an embodiment, when the endoscope tip is inserted deep within a lumen of the patient's body, the user can start from a lower intensity and subsequently instruct the system, via the controller, to increase the intensity level until the light is visible outside and the location of endoscope tip is identified. In such cases, in an embodiment, the controller uses a predefined algorithm to first identify the illuminators for which the intensity has to be increased or decreased and accordingly applies specific functions with dynamic function parameters to each illuminators such that the total heat generated by the system remains within threshold limit during the entire process. In this case, the system dynamically calculates and applies the function parameters for each illuminator as the user increases or decreases the required intensity level.

Figure 6:
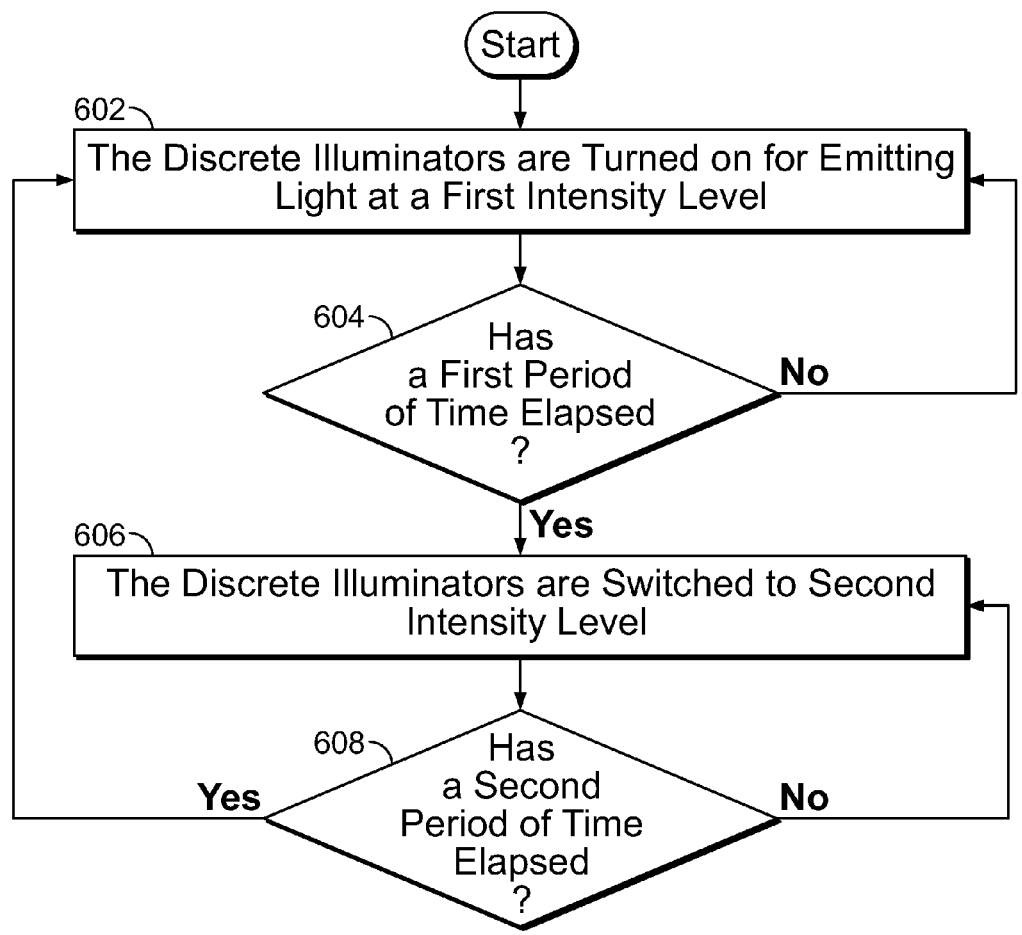
FIG. 6 is a flowchart illustrating an exemplary method of operating the discrete illuminators in a flash mode, in accordance with one embodiment.

FIG. 6 illustrates a general method of operating the discrete illuminators in a flash mode, according to an embodiment. At step 602 the discrete illuminators, which in an embodiment are LEDs, are activated to emit light at a first illumination level. In an embodiment, the first intensity or illumination level is predefined. In an embodiment, the first illumination level is the highest illumination level each discrete LED is capable of emitting. At step 604, the system determines if a first period of time has elapsed. In one embodiment, the first period of time is predefined. The video controller maintains a clock in data communication with a memory and processor. In combination, the video controller times the first illumination level predefined period of time. If the first period of time has not elapsed, the discrete illuminators are kept on and the cycle begins again at step 602. If the first period of time has elapsed, at step 606, the video controller transmits a signal to change the power level of at least one LED to a second illumination level. At step 608, the video controller determines if a second period of time has elapsed. In one embodiment, the second period of time is predefined. If so, after the passage of the second period of time, the power level of at least one LED is modulated again to emit light at the first illumination level. In an embodiment, the first period of time is the same as the second period of time.

In an embodiment, the first and the second periods of time are predefined and stored in the controller memory. In another embodiment, the first and the second periods of time are dynamically calculated by the controller depending on user requirements for the system and application. In another embodiment, the second period of time is shorter than the first period of time. In another embodiment, the first period of time is shorter than the second period of time.

In an embodiment, the first and the second levels of illumination intensity are predefined and stored in the controller memory. In another embodiment, the first and the second illumination intensity levels are dynamically calculated by the controller such that light is visible outside the patient body, while, at the same time, the total heat generated by the LEDs is within a threshold limit. In one embodiment, the first illumination intensity level is higher than the second illumination intensity level. In one embodiment, the second illumination intensity level is higher than the first illumination intensity level. In one embodiment, the first illumination intensity level is higher than the baseline operational intensity level and the second illumination intensity level is lower than the baseline operational intensity level or equal to the baseline illumination intensity level. In an embodiment, the power level of discrete illuminators is simultaneously modulated across different levels of intensity. In some embodiments, a first set of LEDs operates at a higher intensity while a second set of LEDs operates at a baseline operational intensity. In one embodiment, the first predefined intensity is 51 lumens. In one embodiment, the second, intensity ranges from 21 to 45 lumens.

Figure 6A:
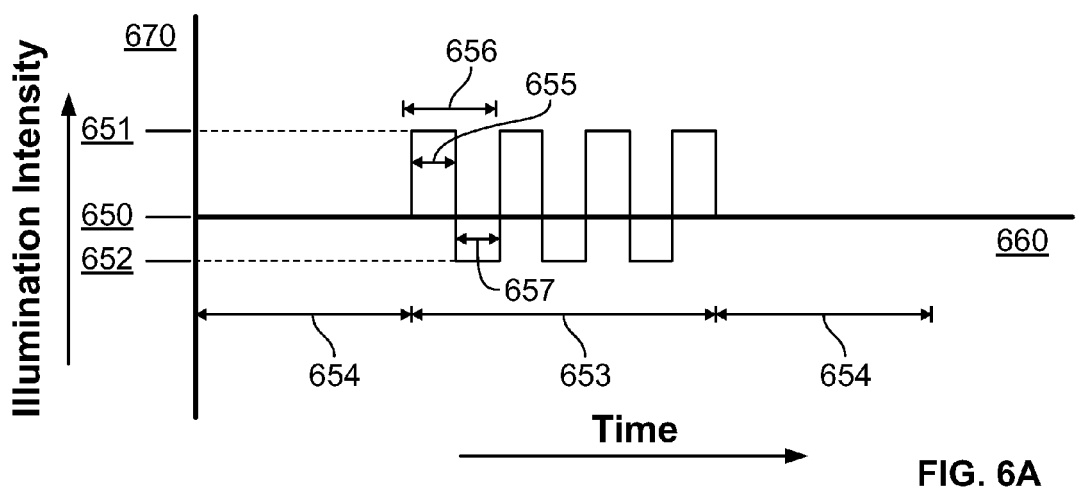
FIG. 6A illustrates an exemplary change in illumination intensity levels of a set of illuminators in accordance with one embodiment of the present specification.

FIG. 6A illustrates an exemplary change in illumination intensity levels of at least one set of illuminators in accordance with one embodiment of the present specification. As shown in FIG. 6A, horizontal axis 660 represents a time period and vertical axis 670 represents an illumination intensity level. Level 650 represents a baseline operational intensity level for the discrete illuminators; level 651 represents a first intensity level at which one or more illuminators are operated during the flash mode; and level 652 represents a second intensity level at which one or more illuminators are operated during flash mode.

Time period 654 corresponds to the duration during which the system is not operated in flash mode and time period 653 corresponds to the duration of the flash mode of operation. First time period 655 represents the duty cycle during which the first intensity level 651 is maintained in each clock cycle while the second time period 657 represents the duty cycle during which the second intensity level 652 is maintained in each clock cycle. Time period 656 represents the total time of each clock cycle during which the intensity level cycles between the first intensity level 651 and the second intensity level 652.

In one embodiment, the first illumination level 651 is shown higher than the baseline operation level and the second illumination level 652 is shown lower than the baseline operation level. In various embodiments, the relative values of intensity levels 651 and 652 can be higher than, lower than, or equal to the baseline operational intensity level 650. In one embodiment, the first time period 655 and second time period 657 are shown as having equal duration. However, in another embodiment, the time periods 655 and 657 can be different.

While in the above example, only one graph is shown to illustrate the change in illumination intensity of the illuminators when operated in flash mode, in various embodiments, different values for intensity or illumination levels 651 and 652; clock time period 656; periods 655, 657, 654, and 653 can be used for each illuminator when operated in flash mode to ensure that the total heat produced during the process is within acceptable threshold levels.

Figure 6B:
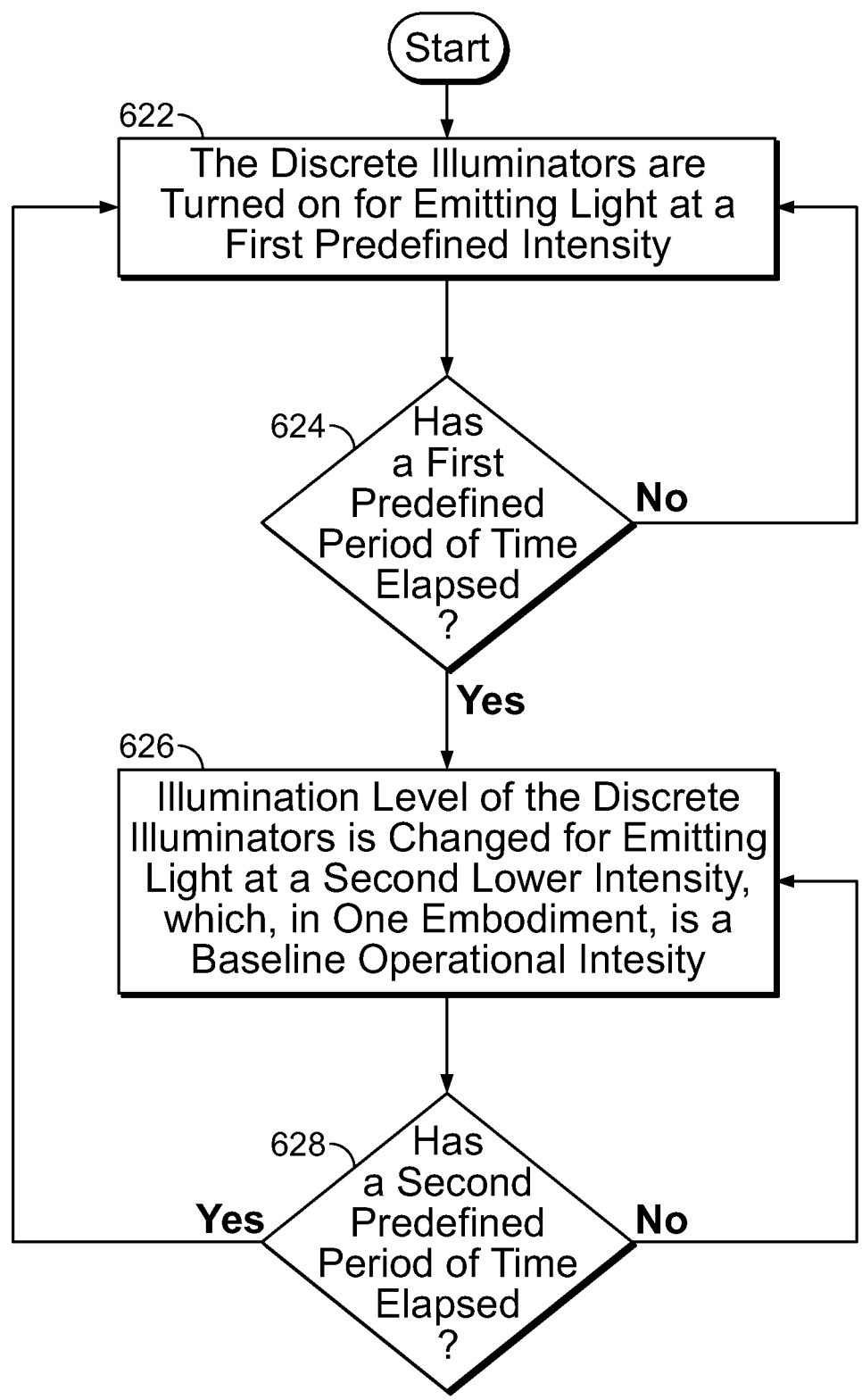
FIG. 6B is a flowchart illustrating another exemplary method of operating the discrete illuminators in a flash mode, in accordance with one embodiment.

FIG. 6B illustrates an exemplary method of operating the discrete illuminators in a flash mode, according to an embodiment. At step 622 the discrete illuminators, which in an embodiment are LEDs, are activated to emit light at a first illumination level or first intensity. At step 624, it is determined if a first predefined period of time has elapsed. At step 626, after the passage of the first predefined period of time, the LEDs are operated to emit light at a second illumination level, or second intensity, which, in one embodiment, is the baseline operational intensity. In an embodiment the second illumination level (baseline operational intensity) is lower than the first illumination level. At step 628, it is determined if a second predefined period of time has elapsed. After the passage of the second predefined period of time the LEDs are operated again to emit light at the first illumination level. In an embodiment, the first predefined period of time is the same as the second predefined period of time whereas in another embodiment, the second predefined period of time is shorter than the first predefined period of time. In one embodiment, the first illumination level is 51 lumens. In one embodiment, the second illumination level is 21 lumens.

Figure 6C:
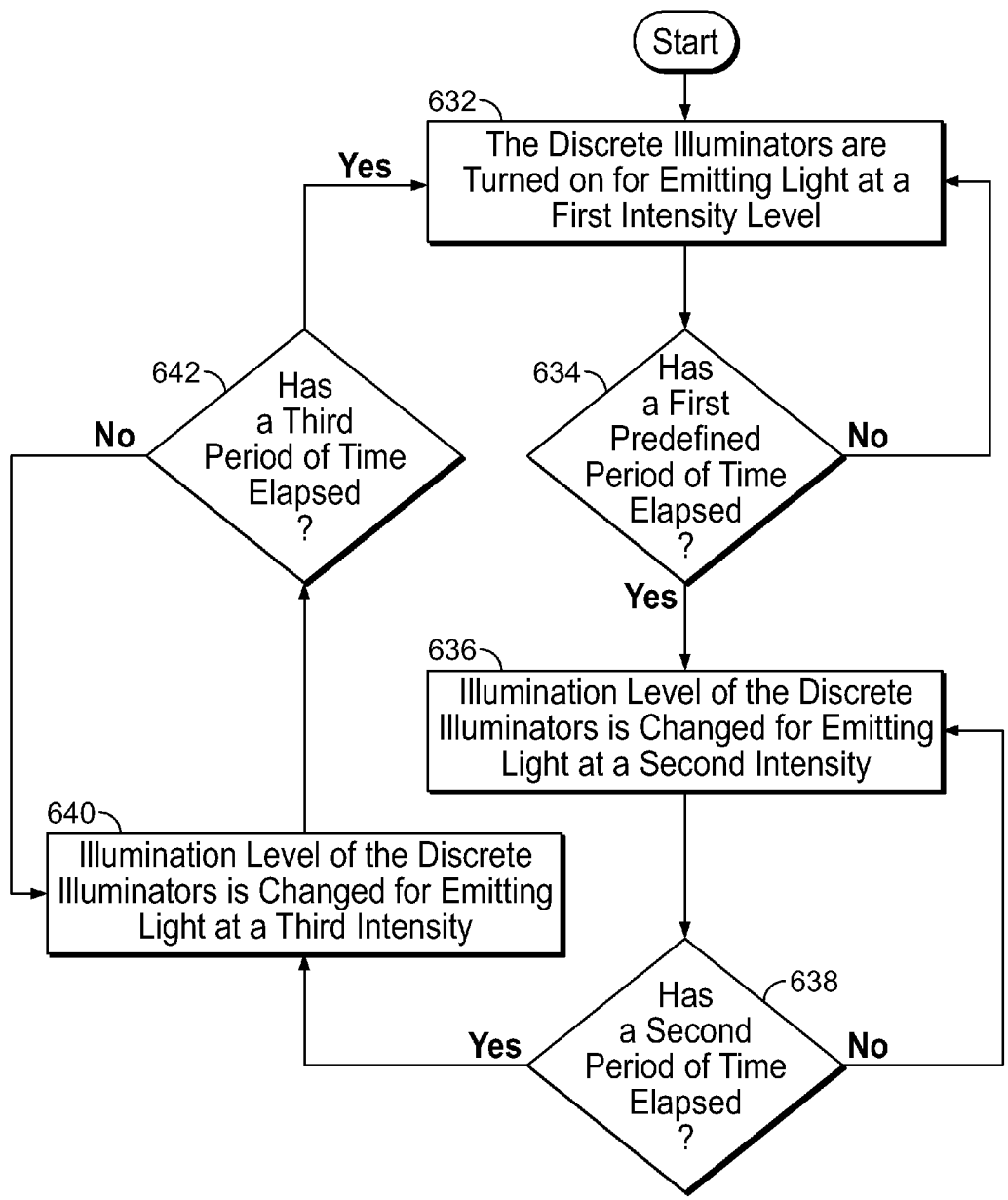
FIG. 6C is a flowchart illustrating yet another exemplary method of operating the discrete illuminators in a flash mode, in accordance with one embodiment.

FIG. 6C illustrates yet another exemplary method of operating the discrete illuminators in a flash mode, according to an embodiment. In this embodiment, the intensity of the discrete illuminators varies between three different levels. At step 632 the discrete illuminators, which in an embodiment are LEDs, are illuminated to emit light at a first illumination level or first intensity level. At step 634, it is determined if a first period of time has elapsed. At step 636, after the passage of the first period of time, the LEDs are operated to emit light at a second illumination level or second intensity level. In an embodiment the second illumination level is lower than the first illumination level. At step 638 it is determined if a second period of time has elapsed. At step 640, after the passage of the second period of time, the LEDs are operated to emit light at a third illumination level or third intensity level. In an embodiment, the third illumination level is lower than the second illumination level. At step 642 it is determined if a third period of time has elapsed. After the passage of the third period of time the LEDs are operated again to emit light at the first illumination level. In an embodiment the first, second and third periods of time are predefined and stored in a controller memory. In an embodiment, the first, second and the third predefined periods of time are the same. One may appreciate that while the above embodiment describes a system wherein the illumination level of discrete illuminators varies between three different levels, one could operate the discrete illuminators at more than three levels of illumination intensity without departing from the spirit and scope of present specification.

Figure 7:
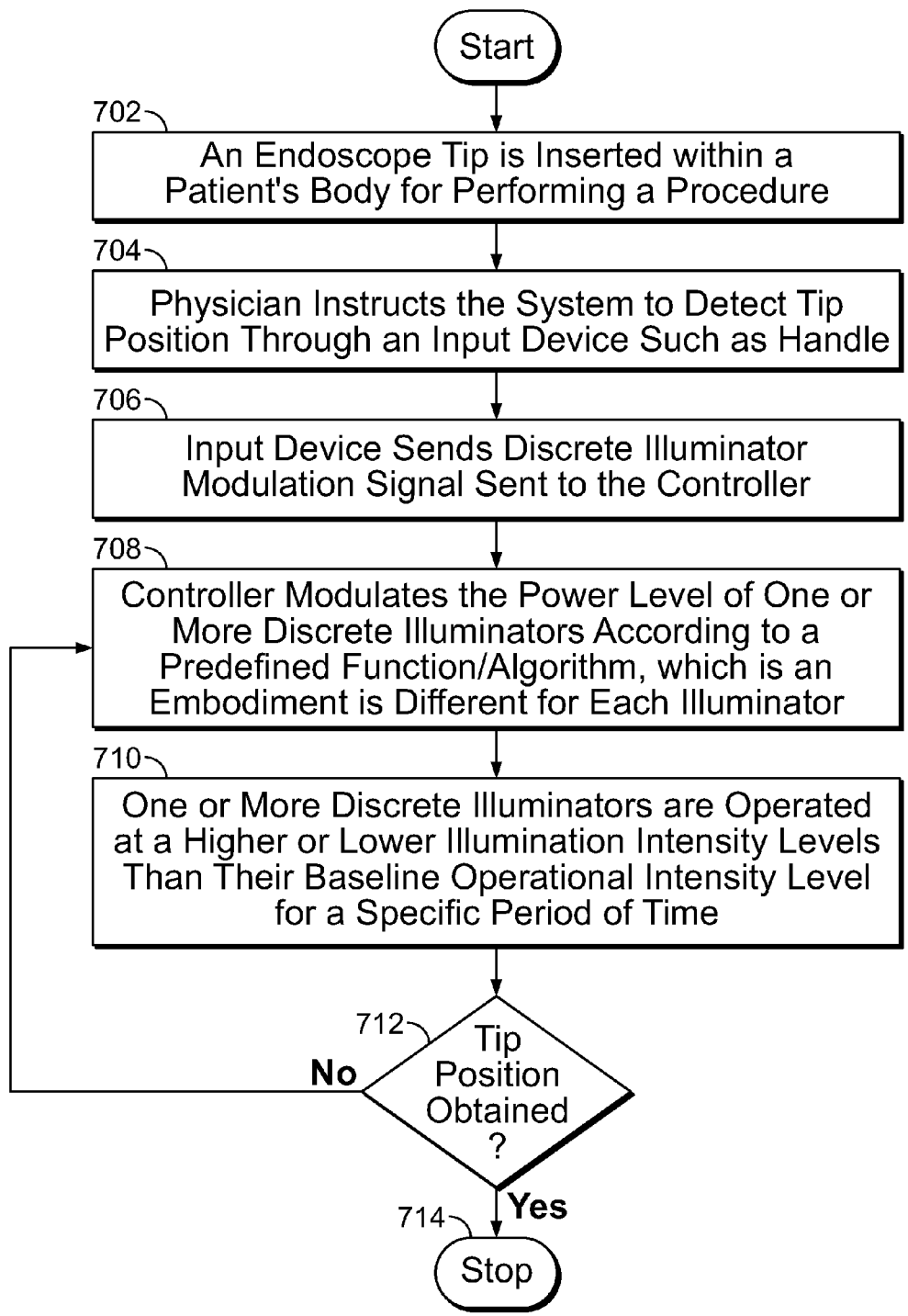
FIG. 7 is a flowchart illustrating a method for obtaining a position of an endoscope tip within a patient's body from outside the body by modulating the power level of discrete illuminators, in accordance with one embodiment.

FIG. 7 is a flowchart illustrating a method for obtaining a position of an endoscope tip within a patient's body from outside the body in accordance with an embodiment of the present specification. In one embodiment, a physician operates a handle portion of an endoscope having a tip with discrete illuminators positioned thereupon (described above with reference to FIG. 1). At step 702, the physician inserts the endoscope tip inside the patient's body for performing a procedure using controls on the handle portion. At step 704, physician instructs the system to detect the tip position of the endoscope by providing an input through an input device such the handle or an external keyboard or touchscreen display. In an embodiment, the handle portion of the endoscope comprises one or more designated buttons which when toggled or otherwise activated by the physician cause a discrete illuminator modulation signal to be sent to an external controller as shown in step 706. In one embodiment, the discrete illuminator modulation signal causes the controller to modulate the power level of one or more discrete illuminators according to a predefined function.

For example, a first signal (caused by a first button press on the handle) may cause the controller to increase the power level of each discrete illuminator, thereby increasing the intensity of the emitted light, for a first period of time and then decrease the power level of each discrete illuminator for a second period of time. It should be appreciated that any of the above described intensity functions could be deployed. As the discrete illuminator intensity varies, the physician observes the patient's skin to see the endoscope tip, which may be visible through the patient's body because of the higher discrete illuminator intensity level.

Accordingly, at step 708, on receiving the discrete illuminator modulation signal, the controller modulates the power level of one or more discrete illuminators in accordance with a predefined function that governs the manner in which the intensity levels of any illuminator is to be modulated.

In one embodiment, the controller applies same function to all the illuminators. In an alternate embodiment, the controller applies a different function to each illuminator. At step 710, based on the modulation, one or more discrete illuminators operate at one or more intensity levels which may be different than their baseline operational intensity level for specific periods of time. In above embodiment, the modulation is performed in such a manner that the light emitted by one or more illuminators is visible outside the patient body which helps in tracking the position of endoscope tip while keeping the total heat generated by the system within a threshold limit. At step 712, the physician determines if the tip position of the endoscope has been located. If the tip position has been located, the process is complete. If the tip position has not been located, the process, via inputs to the controller, begins again at step 708.

In various alternate embodiments of the present specification, LEDs are configured to have multiple intensity states, provided that the total heat output, relative to operating the LED at full brightness 100% of the time, is reduced. At higher intensities, the heat increases relatively to the constant light intensity.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive.

We claim:

1. A system for managing heat generated in a tip of an endo scope, comprising:
   a controller external to the endoscope, wherein said controller comprises a memory for storing programmatic functions and a processor for executing said programmatic functions;
   an input device in data communication with said controller, wherein said input device is adapted to receive data indicative of a programmatic function and wherein said input device is configured to communicate said data indicative of a programmatic function to the controller; and
   a plurality of discrete illuminators positioned within said tip and in electrical communication with said controller, wherein each of said plurality of discrete illuminators emits an amount of visible light and wherein said controller executes a programmatic function based upon said data indicative of a programmatic function that causes at least one of said plurality of discrete illuminators to operate in a first mode and a second mode, wherein, in said first mode, the at least one of said plurality of discrete illuminators emits said visible light at a baseline illumination level that is greater than zero and wherein, in said second mode, the at least one of said plurality of discrete illuminators emits said visible light at a first illumination level that is greater than the baseline illumination level for a first period of time and at a second illumination level that is greater than zero but less than the baseline illumination level for a second period of time.

2. The system of claim 1 wherein the first illumination level causes at least one of said plurality of discrete illuminators to emit an amount of visible light in a range of greater than 40 lumens.

3. The system of claim 2 wherein the second illumination level causes at least one of said plurality of discrete illuminators to emit an amount of visible light in a range less than 40 lumens.

4. The system of claim 1 wherein the programmatic function defines a duty cycle for the at least one of said plurality of discrete illuminators, and, wherein during 30% of said duty cycle, the programmatic function defines the first illumination level to be greater than 40 lumens.

5. The system of claim 4 wherein during 70% of said duty cycle, the programmatic function defines the second illumination level to be less than 40 lumens.

6. The system of claim 1 wherein the input device is at least one of a touch screen display, a button on a handle of the endoscope, a keypad, or a mobile device.

7. The system of claim 1 wherein the programmatic function defines, for the at least one of said plurality of discrete illuminators, the first illumination level to be in a range of 45-55 lumens for the first period of time and the second illumination level to be in a range of 15-25 lumens for the second period of time.

8. The system of claim 1 wherein the programmatic function defines, for at least one of said plurality of discrete illuminators, the baseline illumination level to be in a range of 20-35 lumens.

9. The system as claimed in claim 1, wherein, in said second mode, the at least one of said plurality of discrete illuminators is operated to emit light having an intensity of at least 15 lumens for a maximum of 60 milliamperes current for a duration of 3 to 15 seconds with pulses of 10 to 50 milliseconds in duty cycle ranging between 10% to 50%.

10. The system as claimed in claim 1, wherein a same programmatic function is applied to each of the plurality of discrete illuminators in the endoscope tip.

11. A method of tracking a position of an endoscope tip within a human body, wherein the endoscope tip comprises one or more viewing elements and one or more discrete illuminators for illuminating fields of view of the viewing elements, wherein each viewing element is associated with at least one discrete illuminator, the method comprising:
   providing a controller external to the endoscope, wherein said controller comprises a memory for storing programmatic functions and a processor for executing said programmatic functions;
   providing an input device in data communication with said controller, wherein said input device is adapted to receive data indicative of a programmatic function and wherein said input device is configured to communicate said data indicative of a programmatic function to the controller; and
   providing a plurality of discrete illuminators positioned within said tip and in electrical communication with said controller, wherein each of said plurality of discrete illuminators emits an amount of visible light and wherein said controller executes a programmatic function based upon said data indicative of a programmatic function that causes at least one of said plurality of discrete illuminators to operate in a first mode and a second mode, wherein, in said first mode, the at least one of said plurality of discrete illuminators emits said visible light at a baseline level that is greater than zero and wherein, in said second mode, the at least one of said plurality of discrete illuminators emits said visible light, for a first period of time, at a first power level that is greater than the baseline level for a first period of time and emits said visible light, for a second period of time, at a second power level that is greater than zero but less than the baseline level.

12. The method of claim 11 wherein the first power level causes at least one of said plurality of discrete illuminators to emit an amount of visible light in a range of greater than 40 lumens.

13. The method of claim 12 wherein the second power level causes the at least one of said plurality of discrete illuminators to emit an amount of visible light in a range less than 40 lumens.

14. The method of claim 11 wherein the programmatic function defines a duty cycle for the at least one of said plurality of discrete illuminators, and, wherein during 30% of said duty cycle, the programmatic function defines the first power level to be an amount that generates an illumination of greater than 40 lumens.

15. The method of claim 14 wherein during 70% of said duty cycle, the programmatic function defines the second power level to be an amount that generates an illumination of less than 40 lumens.

16. The method of claim 11 wherein the input device is at least one of a touch screen display, a button on a handle of the endoscope, a keypad, or a mobile device.

17. The method of claim 11 wherein the programmatic function defines, for the at least one of said plurality of discrete illuminators, the first power level to be an amount that causes the at least one of said plurality of discrete illuminators to emit an amount of visible light in a range of 45-55 lumens for the first period of time and the second power level to be an amount that causes the at least one of said plurality of discrete illuminators to emit an amount of visible light in a range of 15-25 lumens for the second period of time.

18. The method of claim 11 wherein the programmatic function defines, for the at least one of said plurality of discrete illuminators, the baseline level to be in a range of 20-35 lumens.

19. The method of claim 11, wherein, in said second mode, the at least one of said plurality of discrete illuminators is operated to emit light having an intensity of at least 15 lumens for a maximum of 60 milliamperes current for a duration of 3 to 15 seconds with pulses of 10 to 50 milliseconds in duty cycle ranging between 10% to 50%.

20. The method of claim 11, wherein a same programmatic function is applied to each of the plurality of discrete illuminators in the endoscope tip.

* * * * *